United States Patent
Fancher

[11] 3,965,137
[45] June 22, 1976

[54] THIOCYANO XANTHATES

[75] Inventor: Llewellyn W. Fancher, Orinda, Calif.

[73] Assignee: Stauffer Chemical Company, Westport, Conn.

[22] Filed: Mar. 31, 1975

[21] Appl. No.: 561,951

Related U.S. Application Data

[63] Continuation-in-part of Ser. No. 466,106, May 2, 1974, abandoned.

[52] U.S. Cl. .................................. 260/454; 71/67; 424/302; 260/455 B
[51] Int. Cl.² ............. C07C 161/02; C07C 155/06; C07C 155/08
[58] Field of Search .................................. 260/454

[56] References Cited
UNITED STATES PATENTS

| | | | |
|---|---|---|---|
| 3,141,818 | 7/1964 | Stephens et al. | 260/454 |
| 3,197,494 | 7/1965 | Strycker | 260/454 |
| 3,197,495 | 7/1965 | Strycker | 260/454 |
| 3,324,134 | 6/1967 | Wakeman | 260/454 |
| 3,830,829 | 8/1974 | Olan | 260/454 |

FOREIGN PATENTS OR APPLICATIONS

| | | | |
|---|---|---|---|
| 445,375 | 6/1969 | Japan | 260/454 |

*Primary Examiner*—Elbert L. Roberts
*Assistant Examiner*—D. R. Phillips
*Attorney, Agent, or Firm*—Michael J. Bradley

[57] ABSTRACT

This invention relates to the utility of certain thiocyano xanthates as biocidal and miticidal agents having the formula

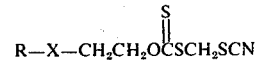

wherein X equals —O or —S; and R is selected from the group consisting of alkyl containing from 1 to 7 carbon atoms, alkoxyalkyl containing from 2 to 7 carbon atoms, napthyl, phenyl and substituted phenyl wherein the substituents can be selected from the group consisting of alkyl containing from 1 to 3 carbon atoms, alkoxy containing from 1 to 3 carbon atoms, halogen and nitro. The compounds of this invention are biocidally and miticidally active.

19 Claims, No Drawings

THIOCYANO XANTHATES

CROSS REFERENCE TO RELATED APPLICATION

This application is a Continuation-In-Part of copending application Ser. No. 466,106 filed May 2, 1974, now abandoned.

DETAILED DESCRIPTION OF THE INVENTION

This invention relates to the utility as biocidal and miticidal agents for control of bacteria, algae, fungi and mites when used in a bactericidally, algaecidally, fungicidally or miticidally effective amount of certain thiocyano xanthates having the formula

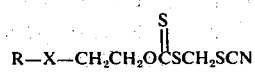

wherein X equals —O or —S; and R is selected from the group consisting of alkyl containing from 1 to 7 carbon atoms, alkoxyalkyl containing from 2 to 7 carbon atoms, napthyl, phenyl and substituted phenyl wherein the substituents can be selected from the group consisting of alkyl containing from 1 to 3 carbon atoms, alkoxy containing from 1 to 3 carbon atoms, halogen and nitro. It has been discovered that these compounds have algaecidal, biocidal and miticidal activity and provide beneficial results in controlling the growth of algae, bacteria and fungi and killing mites.

Controlling the growth of algae, bacteria and fungi by employing the compounds described herein can be accomplished by applying a bactericidally, algaecidally effective amount to the environment in which the growth of algae, bacteria or fungi is encouraged. The compounds may be applied in any environmental area which supports the growth and development of algae, bacteria or fungi. By "controlling" is meant the prevention of the growth of the algae, bacteria or fungi to be controlled.

Miticidal activity can be achieved by applying the compounds to the habitat of the mites in an effective amount to control the mites.

The compounds of this disclosure are prepared by reacting xanthates salts with chloromethylthiocyanate to give the desired product. The generalized equation is:

$$RXCH_2CH_2O\overset{S}{\underset{\|}{C}}S^-M^+ + ClCH_2SCN \rightarrow RXCH_2CH_2O\overset{S}{\underset{\|}{C}}SCH_2SCN + MCl$$

(M+ = sodium + potassium + etc.)

It has been found that the conditions for the reaction are fairly specific in order to produce high purity product. If for example, an excess of the xanthate salt is used an undesireable by-product

is felt to be formed by the following equation:

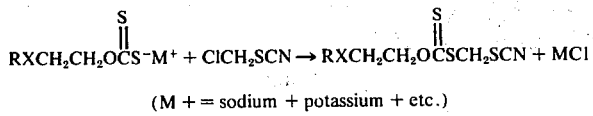

Dimethylformamide has been found to be a good reaction solvent although other non-reactive solvents (such as dioxane, tetrahydrofuran, etc.) could be used. Also iodides have been used as a catalyst for the reaction. The following examples demonstrate the preparation and the utilization of compounds of the present invention.

EXAMPLE 1

Thiocyanomethyl-ethoxyethylxanthate

Ninety and two-tenths grams (90.2 g) (0.835 M) (68.5 ml) of chloromethylthiocyanate, 16.7 g. (0.1 M) of potassium iodide and 400 ml. of dimethyl formamide were mixed with cooling below 20°C. To this mixture was added over a few minutes at 20°C, 156.7 g (0.833 M) of sodium-ethoxy-ethyl xanthate with stirring. Cooling was initiated and the temperature was not allowed to rise above 38°C. After approximately 5 minutes the initial exothemic reaction ceased. The mixture was then stirred at ambient temperature for 2 hours. A mixture of 200 ml. of benzene, 200 ml. of hexane and 1,000 ml. of water were added and well mixed. The aqueous phase was removed and extracted with 100 ml. of hexane. The hexane extract was added to the previous organic phase which was then washed 4 times with 500 ml. portions of water, dried over anhydrous magnesium sulfate, filtered and stripped of solvent under vacuum at less than 65°C and finally stripped on a high vacuum (0.2 mm) diffusion pump at 50°C. The product, a light yellow liquid $N_D^{30}$ 1.5674 weighed 119.7 which was 60.6% of theory. Analysis gave (by G.C.) 89.5 area percent.

EXAMPLE 2

Thiocyanomethylphenoxyethyl xanthate

Eleven and eight-tenths grams (11.8 g) (0.05 M) of sodium-phenoxyethyl xanthate and 1 g. of potassium iodide was added to 25 ml. of dimethylformamide. The mixture was stirred and 4.3 g (0.04 M) (3.3 ml.) of chloromethylthiocyanate was added slowly with stirring and cooling at below 20°C. The mixture was allowed to stand at ambient for three days. Then stirred for two hours and allowed to stand for an additional day. The mixture was diluted with 150 ml. of benzene and washed 3 times with water, dried over $MgSO_4$, filtered and stripped under vacuum. The liquid product $N_D^{30}$ 1.6031 weighed 9.5 g. which was 83% of theory. The structure was confirmed by NMR.

The compounds utilized in this invention and exemplified in the following as the biocidally and miticidally active compounds as examples are as follows:

TABLE I $$RXCH_2CH_2O\overset{\overset{\displaystyle S}{\|}}{C}SCH_2SCN$$

| Compound Number | R | X |
|---|---|---|
| 1 | $C_2H_5-$ | O |
| 2 | phenyl- | O |
| 3 | $CH_3-$ | O |
| 4 | $C_2H_5-$ | S |
| 5 | $C_2H_5OCH_2CH_2-$ | O |
| 6 | $n-C_4H_9-$ | O |
| 7 | $n-C_4H_9OCH_2CH_2-$ | O |
| 8 | 2-chlorophenyl- | O |
| 9 | phenyl- | S |
| 10 | 4-methylphenyl- | O |
| 11 | 4-methoxyphenyl- | O |
| 12 | 2-methylphenyl- | O |
| 13 | 4-chlorophenyl- | O |
| 14 | 4-chlorophenyl- | S |
| 15 | naphthyl- | S |
| 16 | 4-chloro-2-methylphenyl- | O |
| 17 | 4-methylphenyl- | S |
| 18 | 2,4-dichlorophenyl- | O |

The compounds will be hereinafter referred to by compound numbers in the following examples.

EXAMPLE 3

Biocide Testing Procedure

Tubes of sterilized nutrient and malt extract broth are prepared. Aliquots of the toxicant, dissolved in an appropriate solvent, are injected through the stopper, into the broth, to provide concentrations ranging from 50 ppm downward. The test organism is a fungus, *Phoma herbarum*. Three drops of a spore suspension of the fungus are injected into the tubes of malt broth. One week later the growth of the organism is observed and effectiveness of the chemical is recorded as the lowest concentration in ppm which provides 50% inhibition of growth as compared to untreated inoculated tube. The results of these tests are tabulated in Table II.

TABLE II

| | μgm/ml |
|---|---|
| Compound No. 1 | 5 |

EXAMPLE 4

In Vitro Agar Screening Tests

This test measures the bactericidal, fungicidal and algaecidal properties of a compound when in contact with growing bacteria, fungi or algae in an artificial medium. The test is conducted by adding 20 ml. portions of a suitable warm sterile agar solution into 20 × 100 Petri dishes. Then, the text compound, in 0.5% acetone solution, is added to the Petri dishes at levels of 1, 5, 10 and 50 μg/ml. and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to one week depending on the particular organism. The fungi are incubated at 30°C and the bacteria are incubated at 37°C. The algae are incubated at room temperature under artificial light. Nutrient agar is used as the medium in this test for the bacteria. Potato dextrose agar is used as the medium for the fungi with the exception of *Trichophyton mentagrophytes* for which Emmons agar is used. A modified Jack Meyers agar is used for the growth of the algae.

The extent of growth is noted at the end of the incubation period.

Representative organisms used in this test are as follows:

Bacteria

*Bacillus cereus*
*Brevibacterium ammoniagenes*
*Enterobacter aerogenes*
*Escherichia coli*
*Pseudomonas aeruginosa*
*Pseudomonas fluorescens*
*Staphylococcus aureus*

Fungi

*Aspergillus fumigatus*
*Aspergillus niger*
*Aspergillus oryzae*
*Pencillium expansum*
*Pencillium ochra-chloron*
*Pencillium vermiculatum*
*Rhizopus stolonifer*
*Trichoderma sp.*
*Trichophyton mentagrophytes*
*Pencillium italicum*

Algae

*Chlorella pyrenoidosa*
*Euglena gracilis*
*Scenedesmus obliquus*

TABLE III

In Vitro Screening Tests
Minimum Inhibitory Concentration, µg/ml.

| | | Compound Number 1 |
|---|---|---|
| Bacteria | | |
| | Bacillus cereus | >50 |
| | Brevibacterium ammoniagenes | >50 |
| | Enterobacter aerogenes | >50 |
| | Escherichia coli | 25 |
| | Pseudomonas aeruginosa | 50 |
| | Pseudomonas fluorescens | 50 |
| | Staphylococcus aureus | 5 |
| Fungi | | |
| | Aspergillus fumigatus | 5 |
| | Aspergillus niger | 1 |
| | Aspergillus oryzae | (1) |
| | Pencillium expansum | (5) |
| | Pencillium ochra-chloron | (10) |
| | Pencillium vermiculatum | 10 |
| | Rhizopus stolonifer | (1) |
| | Trichoderma sp. | (10) |
| | Trichophyton mentagrophytes | (10) |
| | Penicillium italicum | 1 |
| Algae | | |
| | Chlorella pyrenoidosa | 1 |
| | Euglena gracilis | 1 |
| | Scenedesmus obliquus | 10 |

( )indicates partial control at this concentration
>greater than

EXAMPLE 5

In Vitro Agar Screening Tests

This test measures the bactericidal and fungicidal properties of a compound when in contact with growing bacteria or fungi in an artificial medium. The test is conducted by adding 20 ml. portions of a suitable warm sterile agar solution into 20 × 100 Petri dishes. Then, the test compound, in 0.5% acetone solution, is added to the Petri dishes at levels of 1, 5, 10 and 50 µg/ml. and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to one week depending on the particular organism. The fungi are incubated at 30°C and the bacteria are incubated at 37°C. Nutrient agar is used as the medium in this test for bacteria. Potato dextrose is used as the medium for the fungi.

The extent of growth is noted at the end of the incubation period.

Representative organisms used in this test are as follows:

Bacteria

Escherichia coli
Staphylococcus aureus

Fungi

Aspergillus niger
Pencillium italicum

TABLE IV

In Vitro Screening Tests
Minimum Inhibitory Concentration, µg/ml.

| Compound Number | Bacteria | | Fungi | |
|---|---|---|---|---|
| | E. coli | S. aureus | A. niger | P. italicum |
| 2 | — | 10 | 1.0 | 0.25 |
| 3 | 50 | 50 | 5.0 | 0.5 |
| 4 | 50 | 5 | 5.0 | 0.5 |
| 5 | 25 | 5 | 5.0 | 1.0 |
| 6 | 50 | 5 | 0.5 | 0.5 |
| 7 | — | 5 | 5.0 | 5.0 |
| 8 | — | 10 | 5.0 | 0.5 |
| 9 | — | 5 | 1.0 | 1.0 |
| 10 | — | 10 | 1.0 | 0.25 |
| 11 | 25 | 5 | 1.0 | (0.25) |
| 12 | >50 | 5 | 1.0 | (0.125) |
| 13 | >50 | 5 | 1.0 | (0.5) |
| 14 | >50 | <5 | (1.0) | (1.0) |
| 15 | >50 | (0.25) | (5.0) | 5.0 |
| 16 | >50 | 5 | (0.5) | (0.5) |
| 17 | (50) | 5 | (1.0) | (0.5) |
| 18 | — | 5 | 5.0 | 5.0 |

( )indicates partial control at this concentration
>greater than
<less than

EXAMPLE 6

Sulfate Reducing Bacteria In Vitro Test

This test measures the bactericidal properties of a compound when in contact with a sulfate reducing bacteria, specifically *Desulfovibrio desulfuricans*. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 µg/ml. of solution. An inoculant solution of 0.5 ml. of the growing organism, *Desulfovibrio desulfuricans*, is added to the vials followed by sufficient sterile distilled water to give a total of 10 ml. of solution in the vials. The vials are incubated at room temperature for 3 to 5 days until untreated controls show growth of the organism as indicated by the black color development in the vials.

The following is a summary of the minimum inhibitory concentration necessary to control the organism.

TABLE V

| | µg/ml. Compound Number I |
|---|---|
| Desulfovibrio desulfuricans | 10 |

EXAMPLE 7

Staphylococcus Aureus Use Dilution Test

This test measures the bacteriostatic effectiveness of a particular test compound against *Staphylococcus aureus*.

Tryptic Soy Broth is dispensed aseptically into sterile 13 × 100 mm. clear glass culture tubes. The first tubes receives 3.6 ml. of medium and tubes 2 through 10 receive 2.0 ml. of medium. The test compound is dissolved in acetone to give 10 ml. of a solution of 0.10% of the test compound. Using a sterile syringe, 0.4 ml. of the test compound solution is placed in the first tube containing the 3.6 ml. of sterile broth and mixed thoroughly. This operation is continued through to the tenth tube. From the tenth tube, 2.0 ml. of solution is removed and discarded. Each tube is then innoculated with 0.1 ml. of a 24 hour culture of Staphylococcus aureus in Tryptic Soy Broth, and the mixture is mixed thoroughly using a Vortex mixer. A control is also set up to be sure that the inoculum is viable using a tube of sterile broth contaiining no added toxicant. The tubes are incubated for 24 hours at 37°C. The tubes are then examined to determine growth of the organism in the culture tubes. The minimum concentration in which no growth of the organism occurs is recorded. The following table gives the minimum inhibitory concentration necessary to control the organism:

TABLE VI

| Toxicant | Minimum Inhibitory Concentration *Staphylococcus aureus*, µg/ml. |
|---|---|
| Compound 1 | 50 |

Miticidal Evaluation Tests

The Two-spotted Mite (2-SM) *Tetranychus urticae* (Koch) is subjected to evaluation tests for miticidal activity. Plant Dip Assay on Two-Spotted Mite [*Tetranychus urticae* (Koch)] Pinto Bean plants (Phaseolus sp.) approximately 10 cm tall, are transplanted into sandy loam soil in 3 inch clay pots and thoroughly infested with two-spotted mites of mixed ages and sexes. Twenty-four hours later the infested plants are inverted and dipped for 2–3 seconds in 50-50 acetone-water solutions of the test chemicals. Treated plants are held in the greenhouse, and seven days later mortality is determined for both the adult mites and the nymphs hatching from eggs which were on the plants at the time of treatment. Test concentrations range from 0.05% down to that at which 50% mortality occurs. The values obtained in this test are found in Table VII under the Columns 2SM-PE and 2SM-Eggs.

TABLE VII

| Compound Number | 2-SM PE | 2-SM Eggs |
|---|---|---|
| 1 | .03 | — |
| 3 | .01 | .01 |
| 5 | .03 | .03 |
| 6 | .03 | — |
| 7 | .03 | — |
| 8 | .05 | — |
| 9 | >.05 | >.05 |
| 10 | >.05 | >.05 |
| 11 | .05 | .05 |
| 12 | .01 | .03 |
| 13 | >.05 | >.05 |
| 14 | .008 | .003 |
| 15 | >.05 | >.05 |
| 16 | .05 | >.05 |
| 17 | >.05 | >.05 |

The compounds of this invention are generally embodied into a form suitable for convenient application. For example, the compounds can be embodied into pesticidal compositions which are provided in the form of emulsions, suspensions, solution, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents such as sesame oil, xylene range solvents, heavy petroleum, etc; water; emulsifying agents; surface active agents; talc; pyrophyllite; diatomite; gypsum; clays; propellants, such as dichlorodifluoromethane etc. If desired, however, the active compounds can be applied directly to feedstuffs, seeds, etc. upon which pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

What is claimed is:

1. A compound having the formula

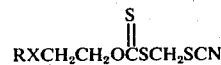

wherein X equals —O or —S; and R is selected from the group consisting of alkyl containing from 1 to 7 carbon atoms, alkoxyalkyl containing from 2 to 7 carbon atoms, napthyl, phenyl and substituted phenyl wherein the substituents can be selected from the group consisting of alkyl containing from 1 to 3 carbon atoms, alkoxy containing from 1 to 3 carbon atoms, halogen and nitro.

2. The compound of claim 1 wherein —R is —$C_2H_5$ and X is O.

3. The compound of claim 1 wherein —R is

and X is O.

4. The compound of claim 1 wherein —R is $CH_3$— and X is O.

5. The compound of claim 1 wherein —R is $C_2H_5$— and X is S.

6. The compound of claim 1 wherein —R is $C_2H_5OCH_2CH_2$— and X is O.

7. The compound of claim 1 wherein —R is n—$C_4H_9$— and X is O.

8. The compound of claim 1 wherein —R is n-$C_4H_9OCH_2CH_2$— and X is O.

9. The compound of claim 1 wherein —R is

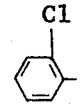

and X is O.

10. The compound of claim 1 wherein —R is

and X is S.

11. The compound of claim 1 wherein —R is

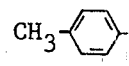

and X is O.

12. The compound of claim 1 wherein —R is

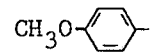

13. The compound of claim 1 wherein —R is
and X is O.
14. The compound of claim 1 wherein —R is
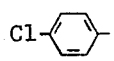
and X is O.
15. The compound of claim 1 wherein —R is
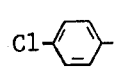
and X is S.
16. The compound of claim 1 wherein —R is
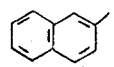
and X is O.
17. The compound of claim 1 wherein —R is
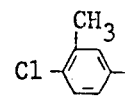
and X is O.
18. The compound of claim 1 wherein —R is
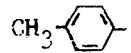
and X is S.
19. The compound of claim 1 wherein —R is
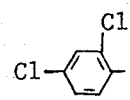
and X is O.
* * * * *